US011105815B2

(12) United States Patent
Goldstein et al.

(10) Patent No.: US 11,105,815 B2
(45) Date of Patent: Aug. 31, 2021

(54) COMPOSITIONS AND METHODS FOR ENHANCING NEURO-REPAIR (71) Applicant: University of Kentucky Research Foundation, Lexington, KY (US)

(72) Inventors: Larry B. Goldstein, Lexington, KY (US); Florin Despa, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 16/395,742

(22) Filed: Apr. 26, 2019

(65) Prior Publication Data
US 2019/0331696 A1    Oct. 31, 2019

Related U.S. Application Data (60) Provisional application No. 62/663,140, filed on Apr. 26, 2018.

(51) Int. Cl.
*G01N 33/53*     (2006.01)
*G01N 33/68*     (2006.01)
*G01N 33/543*    (2006.01)
*A61K 38/28*     (2006.01)
*G01N 1/02*      (2006.01)

(52) U.S. Cl.
CPC ......... *G01N 33/6881* (2013.01); *A61K 38/28* (2013.01); *G01N 33/54306* (2013.01); *G01N 2001/028* (2013.01); *G01N 2333/72* (2013.01); *G01N 2333/908* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,976,853 A | * | 11/1999 | Guthridge | C07H 21/00 435/195 |
| 2003/0166558 A1 | * | 9/2003 | Frangione | C07K 14/47 424/130.1 |
| 2008/0058339 A1 | * | 3/2008 | Brandt | C07D 405/14 514/252.03 |
| 2011/0129522 A1 | | 6/2011 | Mevorat-Kaplan et al. | |

FOREIGN PATENT DOCUMENTS

WO    WO2009034119 A1    3/2009

OTHER PUBLICATIONS

Slevin, John, A Causative Role for Amylin in Diabetic Peripheral Neuropathy, U.S. National Library of Medicine, Clinical Trials, Mar. 29, 2018, pp. 1-8. (Year: 2018).*
EMD Millipore., Human Amylin (Total, 96-Well Plate Cat. #EZHAT-51K, Mar. 2012, pp. 1-11. (Year: 2012).*
Srodulski et al., Neuroinflammation and neurologic deficits in diabetes linked to brain accumulation of amylin, Molecular Neurodegeneration, 2014, 9:30, pp. 1-12. (Year: 2014).*
Van Der Vekiens et al., Human and equine cardiovascular endocrinology: beware to compare, Cardiovascular Endocrinology 2013, vol. 2, No. 4, pp. 67-76 (Year: 2103).*
Torzewski et al., Animal Models of C-Reactive Protein, Hindawl Publishing Corporation, Mediators of Inflammation, vol. 2014, 2014, pp. 1-7. (Year: 2014).*
Banks, et al., Differential Permeability of the Blood-Brain Barrier to Two Pancreatic Peptides: Insulin and Amylin, Peptides, vol. 19, No. 5, pp. 883-889, 1998.
Selvarajah, et al., Central Nervous System Involvement in Diabetes Mellitus, Current Diabetes Reports 2006, 6:431-438.
Jackson, et al., Amylin deposition in the brain: A second amyloid in Alzheimer Disease, Ann Neurol 2013;74:517-526.
Lutz, et al., Amylin at the interface between metabolic and neurodegenerative disorders, Review published: Jun. 16, 2015, pp. 1-13.
Schultz, et al., Amylin alters human brain pericyte viability and NG2 expression, Journal of Cerebral Blood Flow & Metabolism 2017, vol. 37(4) 1470-1482.
Schmidtz, et al., Amylin Antagonists: A Novel Approach in the Treatment of Diabetes, Diabetes, vol. 53, Supplement 3, Dec. 2004, pp. S233-S238.
Hasbak, et al., The Vasorelaxant Effect of Adrenomedullin, Proadrenomedullin N-Terminal 20 Peptide and Amylin in Human Skin, Basic & Clinical Pharmacology & Toxicology 2006, 99, 162-167.
Clementi, et al., Anti-Inflammatory activity of amylin and CGRP in different experimental models of inflammation, Life Sciences, vol. 57, No. 14, pp. PL 193-197, 1995.
Luger, et al., Neuromediators—a critical component of the skin immune system, Journal of Dermatological Science 30 (2002) 87/93.
Yoshimura, et al., Development of 99mTC-Labeled Pyridyl Benzofuran Derivatives to Detect Pancreatic Amylin in Islet Amyloid Model Mice, Bioconjugate Chem. 2016, 27, 1532-1539.
Martinez-Alvarez, et al., Molecular characterization of calcitonin gene-related peptide (CGRP) related peptides (CGRP, amylin, adrenomedullin and adrenomedullin-2/intermedin) in golfish (*Carassius auratus*) Cloning and distribution, Peptides 29 (2008) 15534-1543.
The Human Protein Atlas IAPP (https://www.proteinatlas.org/ENSG00000121351-IAPP/tissue#gene_information), Apr. 20, 2020.
Edwards, et al., Amylin, Life Sciences, vol. 51, pp. 1899-1912, 1992.
Westermark P, Engström U, Johnson KH, Westermark GT, Betsholtz C: Islet amyloid polypeptide: pinpointing amino acid residues linked to amyloid fibril formation. Proc Natl Acad Sci USA 1990, 87(13):5036-5040.

(Continued)

*Primary Examiner* — Gary Counts
(74) *Attorney, Agent, or Firm* — Stiles & Harbison PLLC; Mandy Wilson Decker; Gary Nicholas Stewart (57) ABSTRACT

Methods for determining the presence of pathologic amylin in a subject with diabetes or pre-diabetes are provided herein. The method includes obtaining a skin sample from a subject and determining if there is pathologic amylin present in the skin sample.

5 Claims, 7 Drawing Sheets

(56) References Cited

OTHER PUBLICATIONS

Srodulski S, Sharma S, Bachstetter AB, Brelsfoard JM, Pascual C, Xie S, Saatman KE, Van Eldik LJ, Despa F. Neuroinflammation and neurologic deficits in diabetes linked to brain accumulation of amylin. Mol Neurodegener. 2014; 9 30, pp. 1-12.

Ly H, Verma N, Wu F, Liu M, Saatman KE, Nelson PT, Slevin JT, Goldstein LB, Biessels GJ, Despa F. Brain microvascular injury and white matter disease provoked by diabetes-associated hyperamylinemia. Ann Neurol. 2017;82, 208-222.

Westermark P, Andersson A, Westermark GT. Islet amyloid polypeptide, islet amyloid, and diabetes mellitus. Physiol Rev 2011;91:795-826.

Huang C-J, Haataja L, Gurlo T, Butler AE, Wu X, Soeller WC, Butler PC: Induction of endoplasmic reticulum stress-induced beta-cell apoptosis and accumulation of polyubiquitinated proteins by human islet amyloid polypeptide. Am J Physiol Endocrinol Metab 2007, 293(6):1656-1662.

Verma N, Ly H, Liu M, et al. Intraneuronal amylin deposition, peroxidative membrane injury and increased IL-1beta synthesis in brains of Alzheimer's disease patients with type-2 diabetes and in diabetic HIP rats. J Alzheimers Dis 2016;53:259-272.

Jackson K, Barisone GA, Diaz E, Jin L-W, DeCarli C, and Despa F. Amylin deposition in the brain: a second amyloid in Alzheimer's disease? Ann Neurol 2013; 74: 517-26.

Erickson JR, Pereira L, Ferguson A, Dao K, Despa F, Hart GW, and Bers DM Diabetic Hyperglycemia activates CaMKII and Arrhythmias by O linked Glycosylation. Nature. 2013; 502:372-6.

Despa S, Sharma S, TR Harris, H Dong, N Li, N Chiamvimonvat, H Taegtmeyer, K Margulies, BD Hammock and F Despa, Cardioprotection by controlling hyperamylinemia in a "humanized" diabetic rat model. J Am Heart Assoc 2014 doi: 10.1186/1750-1326-9-30.

\* cited by examiner

COMPOSITIONS AND METHODS FOR ENHANCING NEURO-REPAIR

RELATED APPLICATIONS

This application claims the benefit of U.S. Provisional Application Ser. No. 62/663,140 filed Apr. 26, 2018, the entire disclosure of which is incorporated herein by this reference.

GOVERNMENT INTEREST

This invention was made with government support under grant number R01AG053999 awarded by the National Institutes of Health. The government has certain rights in the invention.

TECHNICAL FIELD

The present invention relates to a method for detecting amylin in the skin of a subject afflicted with pre-diabetes or diabetes and diagnosing the subject with cerebral small vessel disease based on the level of amylin in the skin.

BACKGROUND

Metabolic disorders (obesity, pre-diabetes and type-2 diabetes) increase the risk for cerebral small vessel disease (SVD) and stroke. Distinct from other diabetic complications, glucose dysregulation does not appear to be the primary determinant of progressive end-organ damage to the brain in the setting of diabetes. The pathophysiology underlying slowly progressive functional and structural brain changes in the setting of type-2 diabetes is largely unknown. Type-2 diabetes accounts for about 90% of the cases of diabetes world-wide, and is estimated to affect more than 220 million people. Although it more commonly occurs in adults, type-2 diabetes is becoming more common in children. To date, there is no diagnostic method or treatment of cerebral SVD specific to individuals with diabetes. Data from laboratory models indicate that diabetes-related cerebral SVD may be related to vascular deposition of amylin, which is co-secreted with insulin from the pancreas.

Presently there is no known diagnostic method or treatment for cerebral small vessel disease, particularly in individuals diagnosed with diabetes. The current strategy for identifying cerebral small vessel disease is the use of MRI, which is time and cost prohibitive to implement on a large scale. Furthermore, any subjects that are clinically unstable cannot necessarily be transported to an MRI instrument. In addition, special facilities are required to house MRI equipment which is disadvantageous for persons living in rural communities.

Amylin from rodents does not accumulate in cells and tissues when hypersecreted due to proline substitutions at positions 25, 28, and 291. Therefore, the innate distinctions were exploited between human amylin and rodent amylin variants to assess mechanistically the impact of a "human" amylin dyshomeostasis on skin and brain capillaries in rats expressing human amylin in the pancreas (HIP rats).

The HIP rat is a Sprague-Dawley (SD) rat that expresses human amylin in pancreatic β-cells on the insulin II promoter (bred in-house colony). HIP rats have a ~3-fold increase of amylin secretion, similar to humans with hyper-amylinemia. HIP rats have amylin deposition in pancreas and peripheral organs, including the brain. Quantitative real-time PCR showed no presence of human amylin mRNA in the HIP rat brain, indicating that amylin deposition in the brain comes from the circulation, as observed in humans. Amylin oligomerization and deposition in the pancreas leads to a gradual decline of β-cell mass, increase of non-fasted blood glucose in the 150-200 mg/dl range by ~7-9 mo. of age (pre-diabetes) and onset of full-blown type-2 diabetes (T2D) by 10-12 mo. of age (non-fasted blood glucose >200 mg/dl). Insulin and amylin secretion is maximum at ~8 mo. of age, followed by a decline with the development of T2D (non-fasted blood glucose >200 mg/dl).

Both male and female HIP rats develop overt hyperglycemia and physical deterioration. Symptoms in terminal stages include lethargy and neurological deficits. Sudden death and arrhythmia8 are more frequent in male HIP vs. WT littermate rats. In male HIP rats, hyperglycemia occurs by ~10-12 months of age, whereas female HIP rats show overt hyperglycemia later in life (i.e., 18 months of age). Physical deterioration is milder in females compared to male HIP rats. HIP rats with eight backcrosses to SD rats are used for pathologically targeted interventions to validate proposed mechanisms for aggregated amylin-induced cardiac dysfunction. Age-matched WT littermates are the non-diabetic controls.

SUMMARY

The presently-disclosed subject matter meets some or all of the above-identified needs, as will become evident to those of ordinary skill in the art after a study of information provided in this document.

The present invention provides a way of identifying individuals with pre-diabetes or diabetes who have cerebral SVD. Data from animal models indicate that deposition of amylin in skin capillaries correlates with deposition in brain capillaries. Pre-clinical cerebral SVD is currently identified on neuroimaging (CT or MRI brain scan). Detection of amylin in a skin biopsy would provide a marker of cerebral amylin-related SVD that could obviate the need of neuroimaging in epidemiological studies and provide a means of identifying individuals who might be candidates for yet to be defined therapeutic interventions to block or reverse amylin deposition. The identification of amylin in capillaries comprises contacting a reagent (antibody) that specifically binds amylin to the sample and detecting the amount of amylin bound to the reagent. The extent of amylin deposition in skin capillaries is expected to correlate with the extent of amylin deposition in brain capillaries.

The present invention further provides for screening for agents that prevent or reduce the propensity for cerebral SVD or stroke in an individual who has type-2 diabetes or is prediabetic or suffered a cardiovascular event or kidney failure. The method comprises screening putative agents for their capacity to enhance excretion of circulating aggregated amylin from the body and/or to block or interfere with amylin deposition in capillaries.

The present invention relates to methods of identifying individuals at risk for developing cerebral small vessel disease.

The present invention further relates to methods of identifying individuals at risk for developing structural abnormalities in the brain.

The present invention also includes methods with identify individuals at risk of developing tissue hypoxia and end organ malfunction.

BRIEF DESCRIPTION OF THE DRAWINGS

The presently-disclosed subject matter will be better understood, and features, aspects and advantages other than those set forth above will become apparent when consideration is given to the following detailed description thereof. Such detailed description makes reference to the following drawings, wherein.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding, and no unnecessary limitations are to be understood therefrom.

Definitions

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The term "subject" is used herein to refer to a target of administration, which optionally displays symptoms related to a particular disease, pathological condition, disorder, or the like. Thus, in some embodiments a subject refers to a target that displays symptoms of ischemia and/or brain injury. The subject of the herein disclosed methods can include both human and animal subjects. A subject can be, but is not limited to, vertebrates, such as mammals, fish, birds, reptiles, or amphibians. More specifically, the subject of the herein disclosed methods can include, but is not limited to, a human, non-human primate, cat, dog, deer, bison, horse, pig, rabbit, dog, sheep, goat, cow, cat, guinea pig, or rodent. The term does not denote a particular age or sex. Adult and newborn subjects, as well as fetuses, whether male or female, are intended to be covered. The term "subject" includes human and veterinary subjects.

As used herein, the term "treatment" refers to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. Such a diagnosis can be in reference to a disorder, such as diabetes, and the like, as discussed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular subject will depend upon a variety of factors including the disorder being treated and the severity of the disorder; the specific composition employed; the age, body weight, general health, sex and diet of the subject; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein "pathologic amylin" refers to amylin in an aggregated state, amylin present at concentrations in the skin or vasculature above that of healthy subjects, amyloid, or other dysfunctional states of amylin.

As used herein the term "structural abnormalities of the brain" include expansion of the ventricles, reduction of brain parenchyma size, intracerebral hemorrhages, parenchymal rarefaction, and loss of Myelin Basic Protein immunoreactivity.

There are various diseases associated with structural abnormalities of the brain. It is appreciated in the art that diseases associated with expansion of the ventricles in the brain include but are not limited to: Alzheimer's disease, early aging, and hydrocephalus. It is also appreciated in the art that diseases associated with reduced parenchymal size include but are not limited to: cognitive decline, Alzheimer's disease, and Multiple Sclerosis. It is also appreciated that parenchymal rarefaction is associated with dementia, cognitive impairment, and Alzheimer's disease among others. The loss of Myelin Basic Protein immunoreactivity is associated with demyelinating disorders such as Multiple Sclerosis, Amyotrophic Lateral Sclerosis, among others.

The terms "treat," "treatment," "agent" and the like refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative (prophylatic) treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The terms "diagnose" or "diagnosing" and the like as used herein refer to methods by which the skilled artisan can estimate and even determine whether or not a subject is suffering from a given disease or condition, such as diabetes. Along with diagnosis, clinical "prognosis" or "prognosticating" is also an area of great concern and interest, and the terms "prognose" and the like refer to act of determining the relative risk associated with particular conditions in order to plan the most effective therapy. If an accurate prognosis can be made, appropriate therapy, and in some instances more effective therapy, for the subject can be chosen.

Those of ordinary skill in the art will recognize factors and methods for diagnosing and/or prognosing a subject with diabetes. Factors that can contribute to a diagnosis and/or prognosis of diabetes include circulating glucose levels, glucose metabolism, weight, body mass index, HBA1C, sedentary lifestyles, and other well documented factors.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a neurosphere" includes a plurality of such neurospheres, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, width, length, height, concentration or percentage is meant to encompass variations of in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

Embodiments

In one embodiment of the present invention, the method detects the presence of pathologic amylin in the skin of a pre-diabetic or diabetic subject.

In a further embodiment of the present invention, pathologic amylin is detected in the skin sample using an ELISA.

In another embodiment of the present invention, the skin sample is contacted with a T4157 amylin capture antibody or 4-Hydroxynonenal (4-HNE) antibody.

In a further embodiment of the present invention, the skin sample is further contacted by a detection antibody.

In another embodiment of the present invention, the detection antibody is horseradish peroxidase.

In a further embodiment of the present invention, a direct sandwich ELISA is used to detect pathologic amylin in the skin.

In another embodiment of the present invention, the method can be used to diagnose a subject with cerebral small vessel disease when the presence of pathologic amylin is detected in the skin.

In a further embodiment of the present invention, a subject is administered an effective amount of antithrombotics, insulin, or other treatment to treat cerebral small vessel disease when the method identifies the individual as having cerebral small vessel disease.

In another embodiment of the present invention, a subject diagnosed with cerebral small vessel disease is administered an agent that reduces amylin deposition in the vasculature.

In a further embodiment of the present invention, a subject diagnosed with cerebral small vessel disease is administered an agent that elevates endogenous levels of epoxyeicosanoid acids (EETs).

In another embodiment of the present invention, the subject is diagnosed as being at risk for developing tissue hypoxia when the presence of pathologic amylin is detected in the skin.

In a further embodiment of the present invention, the subject is diagnosed as being at risk for developing end organ malfunction when the presence of pathologic amylin is detected in the skin.

In another embodiment of the present invention, the subject is diagnosed as being at risk for developing Azheimer's Disease, early gaining, hydrocephalus, cognitive decline, Multiple Sclerosis, dementia, and cognitive impairment when the presence of pathologic amylin is detected in the skin.

In another embodiment of the present invention, a method can be used to assess efficacy of an agent that reduces amylin deposition in the vasculature of a subject, by obtaining a first skin sample from the subject before treatment with an effective amount of an agent that reduces amylin deposition in the vasculature, detecting the amount of pathologic amylin present in the first skin sample, treating the subject with an agent that reduces amylin deposition in the vasculature, obtaining a second skin sample from the subject after treatment with an agent that reduces amylin deposition in the vasculature, detecting the amount pathologic amylin present in the second skin sample; and assessing efficacy of the agent based on the amount of amylin present in the second skin sample relative to the first skin sample.

Another embodiment of the present invention includes a kit for detecting the presence of pathologic amylin in a sample, comprising: a T4157 amylin capture antibody or 4-Hydroxynonenal antibody; and a detection antibody.

In a further embodiment of the present invention, the detection antibody in a kit is horseradish peroxidase.

In another embodiment of the present invention, a kit further comprises reagents for performing an ELISA.

In a further embodiment of the present invention, a kit further includes reagents for performing direct sandwich ELISA.

Examples

Materials & Methods

1. Amylin Deposition in Brain and Skin Capillaries

Tissues were processed for co-staining with amylin and collagen IV, as previously described[3]. Antibodies against amylin (1:200, T-4157, Bachem-Peninsula Laboratories, CA) and collagen IV (1:1,000, ab6586, Abcam, MA) were the primary antibodies. The specificity of the amylin antibody in rat tissues was established in previous studies[2,3].

2. Amylin-4-HNE adduct formation in brain capillaries.

The custom-made sandwich ELISA protocol for measuring amylin-4-HNE (4-Hydroxynonenal) adduct formation in skin tissue homogenate involves the following steps:

ELISA protocol for measuring amylin-4-HNE adduct formation in skin tissue homogenate of the present invention involves the following steps:

Coating with Capture Antibody:

Coat the wells of a polystyrene 96 well plate with the T4157 Amylin capture antibody (1:1000) or 4-HNE antibody (1:000) in Bicarbonate buffer (pH 9.6).

Cover the plate with an adhesive plastic and incubate overnight at 4° C.

Remove the coating solution and wash the plate twice by filling the wells with 300 µl PBS with 30 sec. of soaking. The solutions or washes are removed flicking the plate over a sink. The remaining drops are removed by patting the plate on a paper towel.

Blocking and Adding Samples:

Block the remaining protein-binding sites in the coated wells by adding 300 nl blocking buffer (3% BSA prepared in 1×PBS).

Cover the plate with an adhesive plastic and incubate the plate for at least 1-2 hrs at room temperature.

Wash the plate 2 times with PBS with 0.05% Tween®-20 (Polyethylene glycol sorbitan monolaurate) followed by one times with PBS only.

Add 100 µl of appropriately diluted samples to each well in duplicate. Standard and blank must be run with the same plate. Incubate the plate for 4° C. overnight.

Remove the samples and wash the plate three times with 1×PBS with 0.05% Tween®-20 (Polyethylene glycol sorbitan monolaurate) followed by one times with PBS only.

Incubation with Detection Antibody:

Add 100 µl of detection antibody (HRP conjugated amylin (1:2000) or for HRP 4-HNE (1:10000)) prepared in blocking buffer (1% BSA prepared in 1×PBS) in appropriate dilution to each well.

Cover the plate with an adhesive plastic and incubate for 1-2 hrs at room temperature.

Wash the plate five times with PBST (1×PBS with 0.05% Tween®-20 (Polyethylene glycol sorbitan monolaurate) 300 µl per well followed by 1×PBS 300 µl per well.

Detection:

Add TMB (3,3',5,5'-Tetramethylbenzidine) 100 µl per well and incubate for 15-30 min at room temperature.

Add stop solution 50 µl per well.

Immediately take O. D. at 450 nm.

The step involved in sample dilution is important as sample O.D. should come within the range of the standard. Using the direct sandwich ELISA has an advantage over the other commercially available indirect and competitive ELISA where in these commercially available ELISA, detection generate higher levels of signal that may also result in elevated background signal which reduces net specific signal levels.

Results

1. Amylin Deposition in Brain and Skin Capillaries

Figure 1:
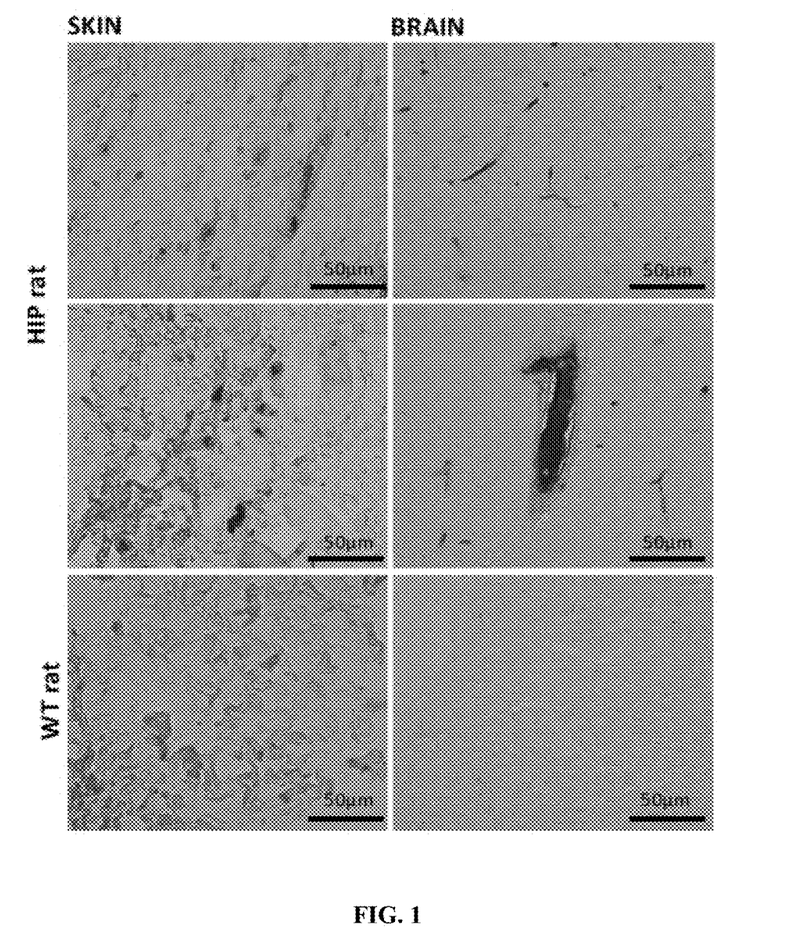
FIG. 1 shows Immunohistochemistry (IHC) for human amylin and collagen IV in skin and brain section from WT and HIP rats Brown: Human amylin; green: Collagen IV; Objective 40×.

Co-staining for amylin and collagen IV, a component of the basement membrane structure, showed amylin deposition in capillaries, in HIP rats (FIG. 1). Tissues were processed as previously described[3]. Antibodies against amylin (1:200, T-4157, Bachem-Peninsula Laboratories, CA) and collagen IV (1:1,000, ab6586, Abcam, MA) were the primary antibodies. The specificity of the amylin antibody in rat tissues was established in previous studies[2,3].

Figure 2:
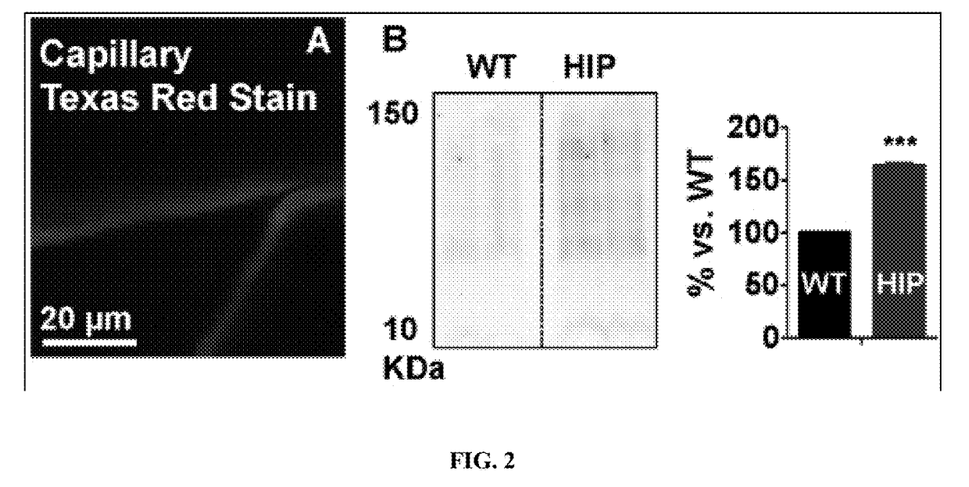
FIG. 2 shows Brain capillaries isolated from HIP rats (A). Incorporated amylin was measured in protein homogenates from capillaries isolated from HIP rats and WT rats (B).

Next, whether amylin incorporates in blood vessel walls was tested. Capillaries isolated from diabetic HIP rats (stained by Texas Red; FIG. 2A) showed elevated levels of incorporated aggregated amylin (FIG. 2B). The results indicate that circulating aggregated amylin infiltrates in the cerebrovasculature.

Figure 3:
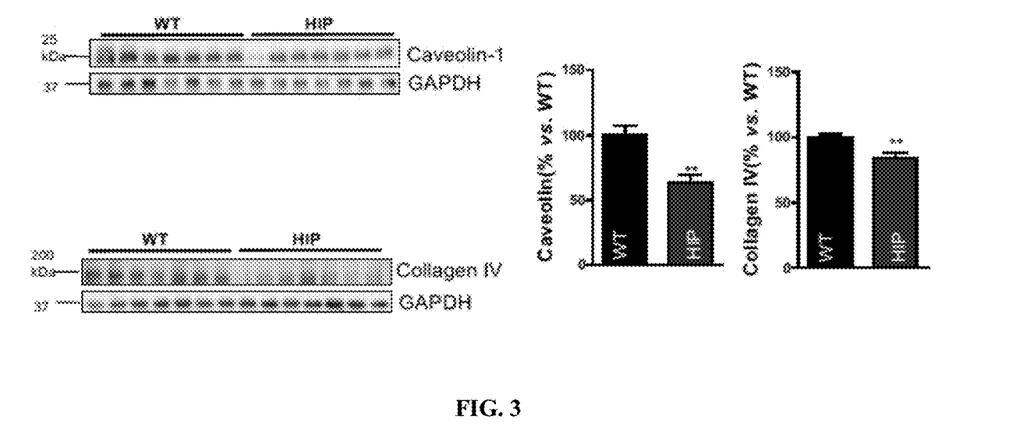
FIG. 3 shows accumulation of amylin in capillaries is associated with depletion of both caveolin-1 and collagen.
Figure 4:
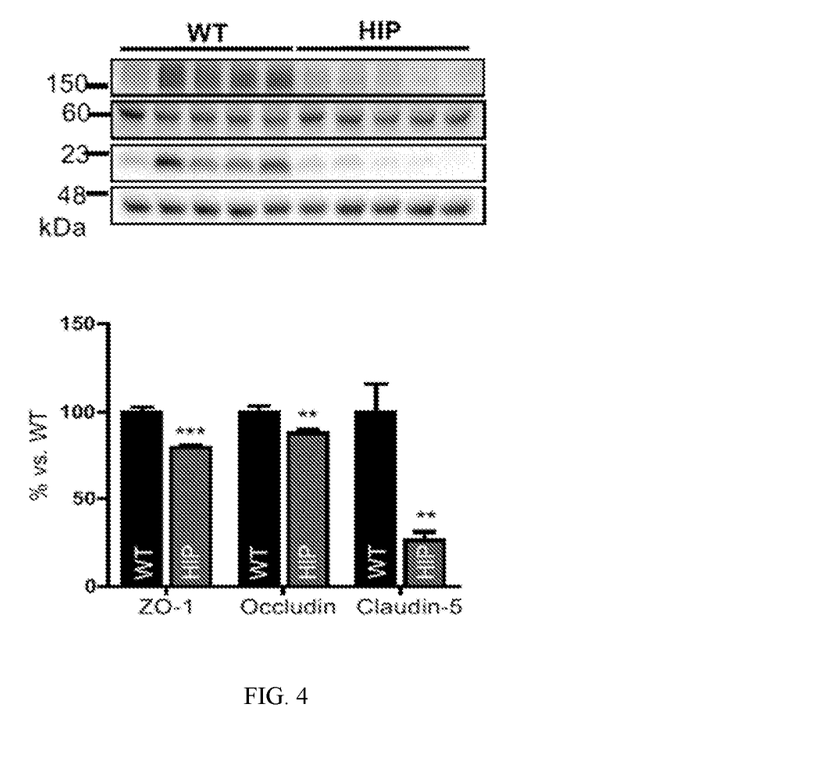
FIG. 4 shows that vascular amylin deposition degrades tight junction components.

The presence of amylin deposits in capillary beds prompted us to assess the stability and integrity of the capillary walls. Capillaries from HIP and WT rat brains were isolated and tested for incorporated amylin, protein levels of collagen IV, caveolin-1 (a protein that is abundant in endothelial cells) and tight junction components (claudin-5, occludin and ZO-1 adapter protein). Consistent with the immunohistochemical results (FIG. 1), capillaries from HIP rats had elevated concentration of amylin. Accumulation of amylin in capillaries was associated with depletion of both caveolin-1 and collagen (FIG. 3), which indicates altered capillary stability. The levels of claudin, occludin and ZO adapter proteins were lower in capillaries from HIP rats compared to WT littermates (FIG. 4) suggesting altered structural integrity of tight junctions in HIP rat capillaries.

2. Amylin-4-HNE Adduct Formation in Brain Capillaries.

Figure 5:
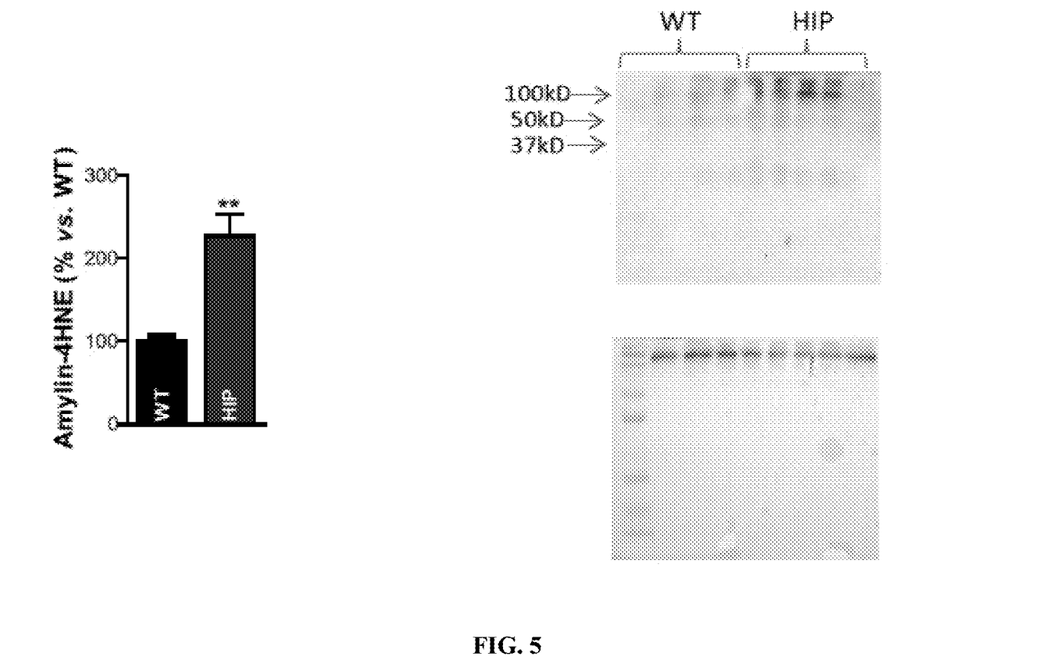
FIG. 5 shows amylin-4HNE adduct formation in the skin.

To demonstrate that amylin incorporation in capillaries negatively affect the stability of cellular membranes, the formation of adducts of amylin with 4-HNE, a marker of membrane peroxidative injury was tested (FIG. 5). There is no commercially available ELISA to measure amylin-4-HNE adduct formation. The custom-made sandwich ELISA protocol of the present invention for measuring amylin-4-HNE adduct formation in skin tissue homogenate was used.

3. Treatment.

Figure 6:
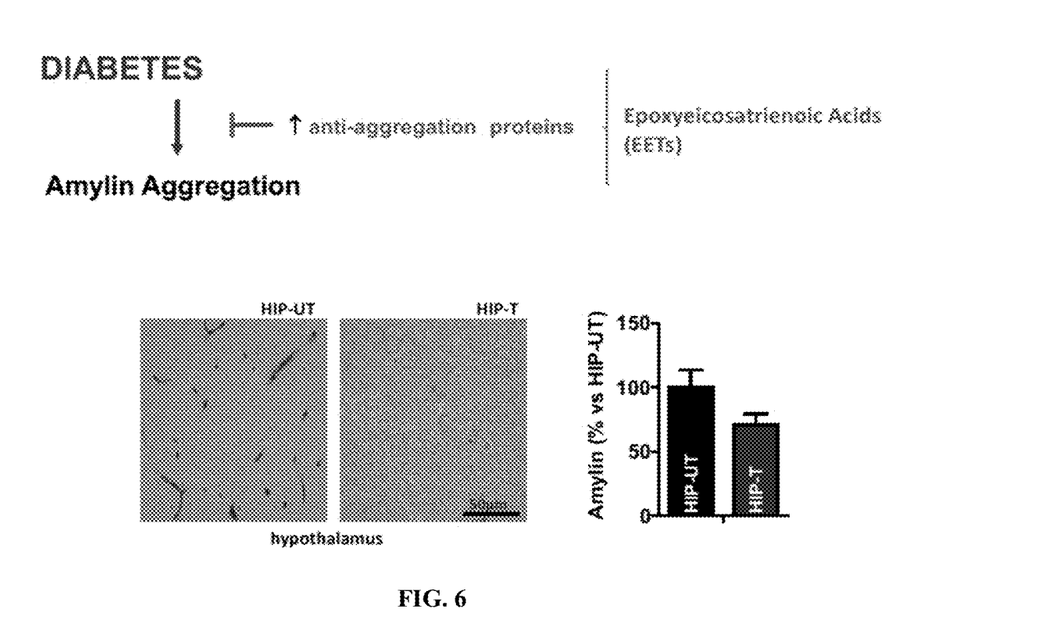
FIG. 6 shows a therapeutic strategy to reduce amylin deposition in capillaries.
Figure 7:
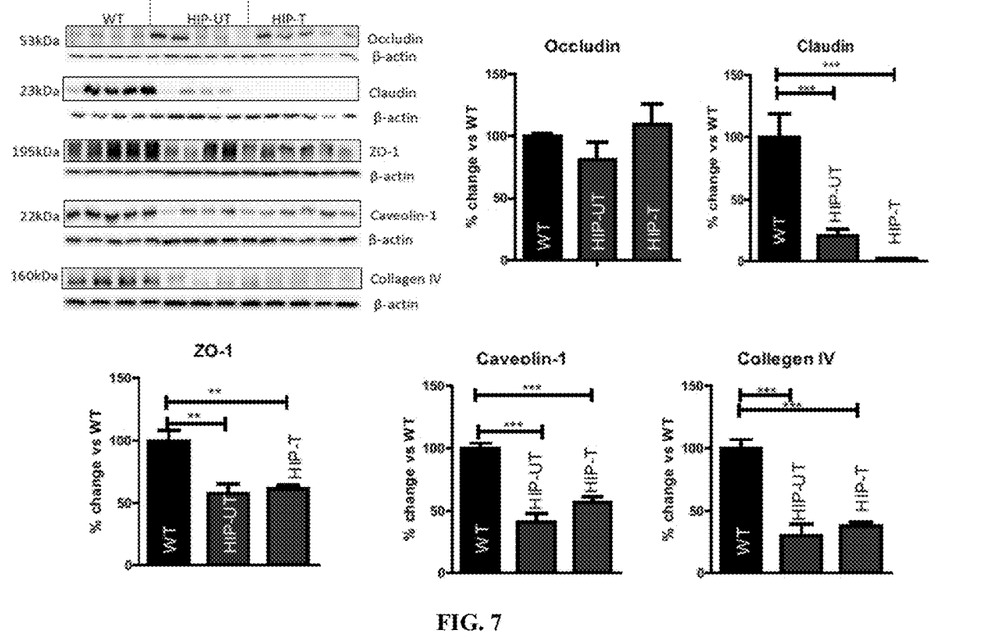
FIG. 7 shows western blots for tight junction protein, caveolin-1 and collagen IV in brain capillaries.

To reduce incorporation of amylin in capillaries in HIP rats, the endogenous levels of epoxyeicosanoid acids (EETs) were pharmacologically elevated, metabolites that bear anti-aggregation properties[9]. Treatment significantly lowered amylin deposition in brain capillaries (FIG. 6), which improved capillary stability (FIG. 7).

4. Amylin Deposition in Brain Capillaries and Skin Capillaries Correlates with the Development of Cerebral Small Vessel Disease.

Figure 8:
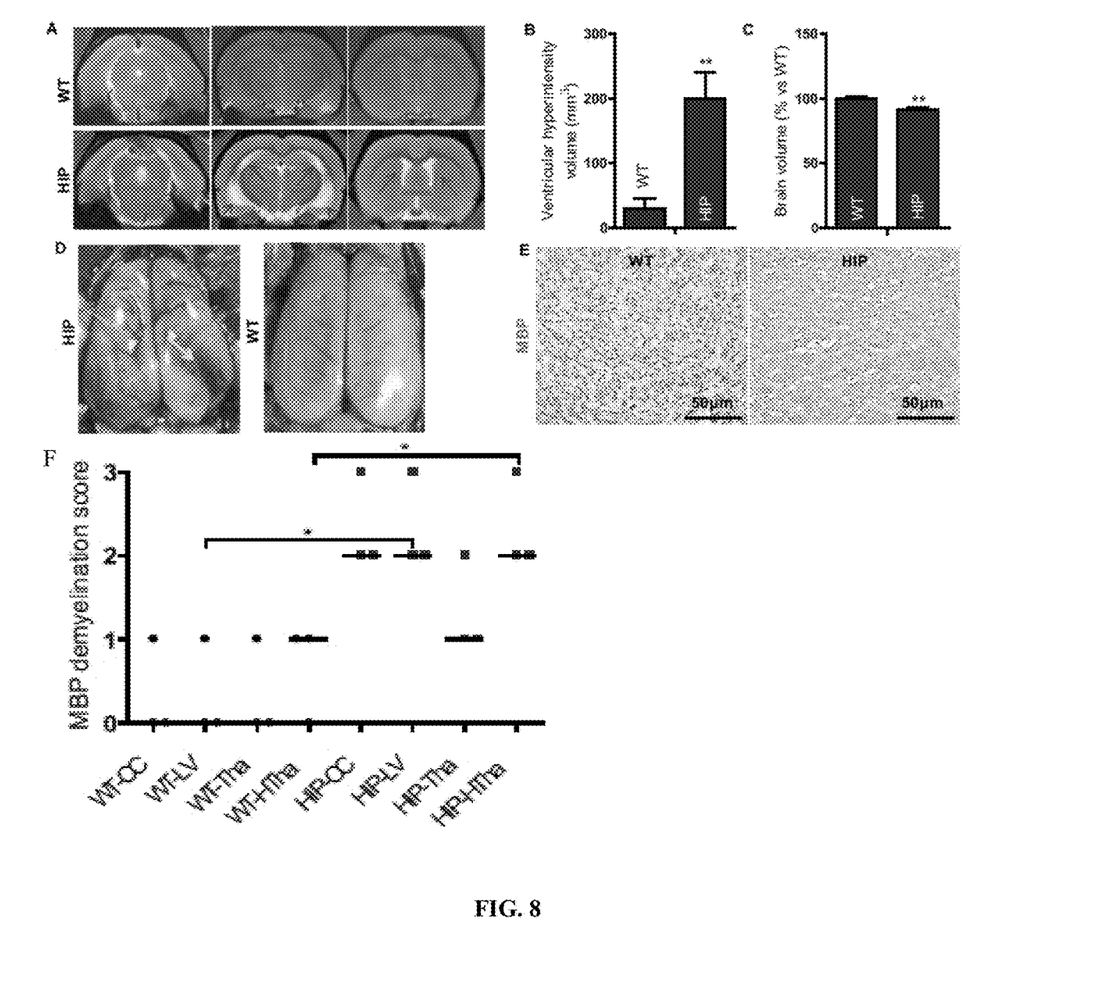
FIG. 8 shows (A) Coronal T2-weighted MR images of HIP rats vs. WT littermates. Hyperintensity areas (1) in the lateral hippocampus and temporal horns of HIP rats reflect extracellular fluid accumulation. (B,C) Volumes of ventricles and brain parenchyma in HIP rats and WT littermates. (D) Intracerebral hemorrhage (↑) in HIP rats. (E) IHC analysis of myelin basic protein (MBP) in the hypothalamus (htha) of a HIP rat vs. a WT littermate. (F) Analysis (graph) of MBP level in HIP and WT brain white matter areas (cc—corpus callosum; lv—lateral ventricle area; tha—thalamus; htha—hypothalamus) (n=3)(from Reference 1).

Over-expression (3-fold) of human amylin in rats (HIP rats) dramatically accelerates aging and leads to neurologic deficits, and gait abnormalities. Amylin deposition in capillaries (FIGS. 1 & 2) correlates with structural abnormalities in the brain (FIG. 8). The brains of HIP rats show areas of high T2 signal in the lateral hippo-campus and around the temporal horns of the lateral ventricles (FIG. 8A; arrows) and expansion of the ventricles (FIG. 8B). The volume of brain parenchyma is smaller in HIP rats compared to WT littermates (FIG. 8C). The brains of rats with falls and impaired balance often have intracerebral hemorrhages (arrow; FIG. 8D), which are not found in WT rats. IHC analysis of brain paraffin sections from HIP rats showed parenchymal rarefaction. HIP rat brains had a loss of MBP immunoreactivity compared to brains from control animals (FIG. 8E). Vacuoles were found through the entire HIP rat brains, but not in controls.

5. Amylin Deposition in Skin Capillaries Correlates with Activation of Hypoxia Signaling Pathways.

Figure 9:
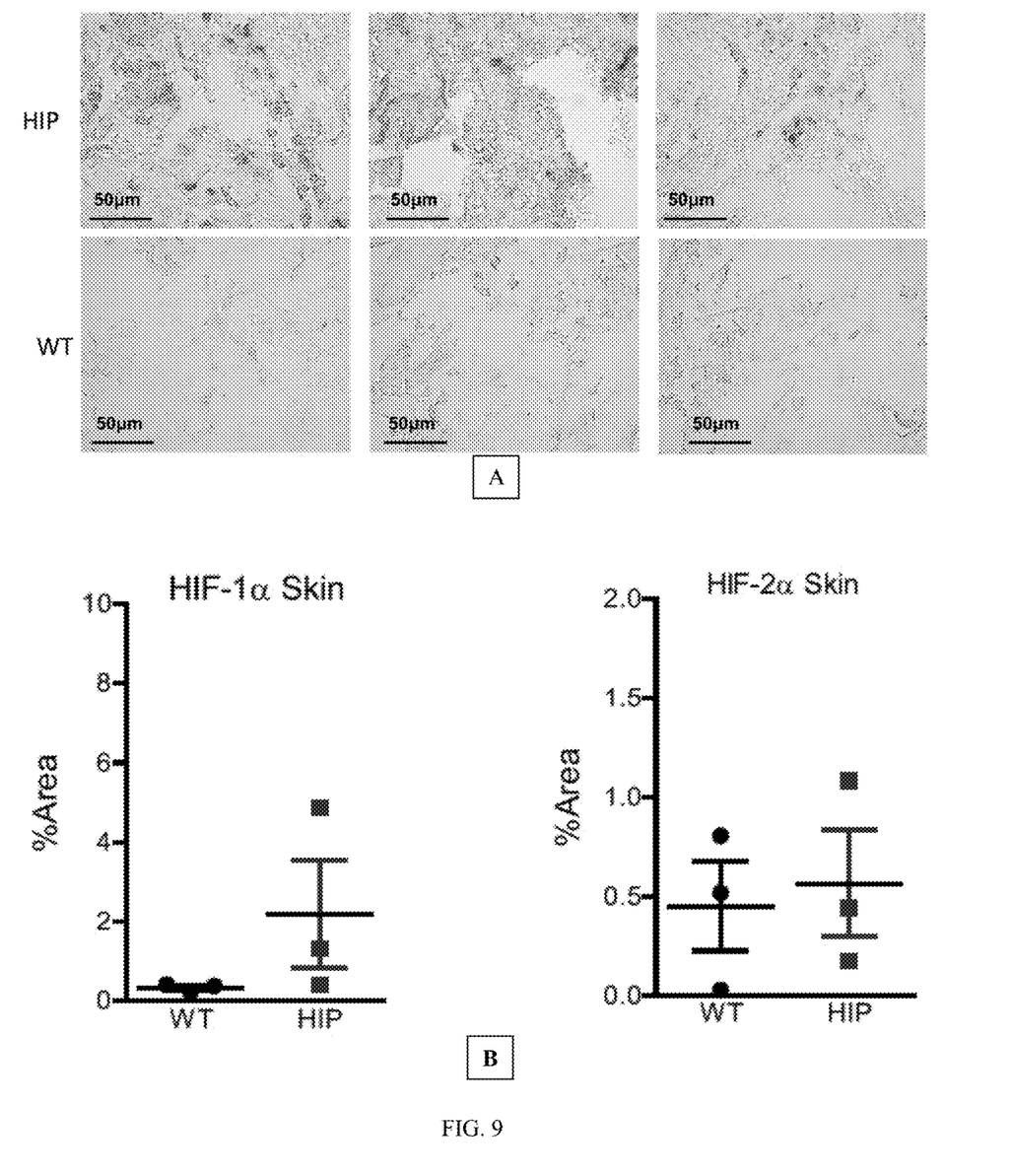
FIG. 9 shows (A) Immunohistochemistry analysis of skin tissue from HIP and WT rats with anti-amylin (brown) and anti-HIF-1α (green) antibodies. (B) The immunoreactivity signal of HIF-1α and HIF-2α in skin tissue from HIP rats compared to WT rats.

Oxygen is essential for cell function and cell survival. In type-2 diabetes and other age-related diseases, the oxygen delivery to cell and tissues declines exacerbating the risk of tissue hypoxia and end organ malfunction. Physiological responses to altered oxygen conditions are primarily driven by the stabilization of the a subunits of the hypoxia-inducible transcription factors HIF-1 and 2. The immunoreactivity signal of HIF-1α is higher in skin tissue from HIP rats compared to WT rats (FIG. 9A). The skin areas positive for HIF-1α activation correlates with amylin deposition in capillaries (FIG. 9B). There is no change in skin tissue HIF-2α immunereactivity.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Westermark P, Engstrom U, Johnson K H, Westermark G T, Betsholtz C: Islet amyloid polypeptide: pinpointing amino acid residues linked to amyloid fibril formation. Proc Natl Acad Sci USA 1990, 87(13):5036-5040.
2. Srodulski S, Sharma S, Bachstetter A B, Brelsford J M, Pascual C, Xie S, Saatman K E, Van Eldik L J, Despa F. Neuroinflammation and neurologic deficits in diabetes linked to brain accumulation of amylin. Mol Neurodegener. 2014; 9 30
3. Ly H, Verma N, Wu F, Liu M, Saatman K E, Nelson P T, Slevin J T, Goldstein L B, Biessels G J, Despa F. Brain microvascular injury and white matter disease provoked by diabetes-associated hyperamylinemia. Ann Neurol. 2017; 82, 208-222
4. Westermark P, Andersson A, Westermark G T. Islet amyloid polypeptide, islet amyloid, and diabetes mellitus. Physiol Rev 2011; 91:795-826
5. Huang C-J, Haataja L, Gurlo T, Butler A E, Wu X, Soeller W C, Butler P C: Induction of endoplasmic reticulum stress-induced beta-cell apoptosis and accumulation of polyubiquitinated proteins by human islet amyloid polypeptide. Am J Physiol Endocrinol Metab 2007, 293(6): 1656-1662.
6. Verma N, Ly H, Liu M, et al. Intraneuronal amylin deposition, peroxidative membrane injury and increased IL-1beta synthesis in brains of Alzheimer's disease patients with type-2 diabetes and in diabetic HIP rats. J Alzheimers Dis 2016; 53:259-272.
7. Jackson K, Barisone G A, Diaz E, Jin L-W, DeCarli C, and Despa F. Amylin deposition in the brain: a second amyloid in Alzheimer's disease? Ann Neurol 2013; 74: 517-26;
8. Erickson J R, Pereira L, Ferguson A, Dao K, Despa F, Hart G W, and Bers D M Diabetic Hyperglycemia activates CaMKII and Arrhythmias by 0 linked Glycosylation. Nature. 2013; 502:372-6.
9. Despa S, Sharma S, TR Harris, H Dong, N Li, N Chiamvimonvat, H Taegtmeyer, K Margulies, BD Hammock and F Despa, Cardioprotection by controlling hyperamylinemia in a "humanized" diabetic rat model. J Am Heart Assoc 2014 doi: 10.1186/1750-1326-9-30;

The invention claimed is:

1. A method of assessing the efficacy of an agent that reduces amylin deposition in the vasculature of a rodent or human subject, comprising:
    a) obtaining a first skin sample from the subject before treatment with an agent that reduces amylin deposition in the vasculature;
    b) detecting an amount of pathologic amylin present in the first skin sample;
    c) treating the subject with the agent that reduces amylin deposition in the vasculature;
    d) obtaining a second skin sample from the subject after treatment with the agent that reduces amylin deposition in the vasculature;
    e) detecting the amount pathologic amylin present in the second skin sample; and
    f) identifying the agent as having efficacy when the amount of amylin present in the second skin sample is less than the amount of amylin present in the first skin sample.

2. The method of claim 1, wherein detecting pathologic amylin in the skin samples is conducted using ELISA or direct sandwich ELISA.

3. The method of claim 2, further comprising contacting the skin samples with a T4157 amylin capture antibody or 4-Hydroxynonenal (4-HNE) antibody.

4. The method of claim 3, further comprising contacting the skin samples with a detection antibody.

5. The method of claim 4, wherein the detection antibody is a horseradish peroxidase (HRP) conjugated antibody.

* * * * *